(12) United States Patent
Sieracki et al.

(10) Patent No.: US 8,345,239 B1
(45) Date of Patent: Jan. 1, 2013

(54) SYSTEM AND METHOD FOR MONITORING BIREFRINGENT PARTICLES IN A FLUID

(75) Inventors: Christian K. Sieracki, Edgecomb, ME (US); William H. Nelson, North Yarmouth, ME (US)

(73) Assignee: Fluid Imaging Technologies, Inc., Yarmouth, NE (US)

( * ) Notice: Subject to any disclaimer, the term of this patent is extended or adjusted under 35 U.S.C. 154(b) by 609 days.

(21) Appl. No.: 12/535,536

(22) Filed: Aug. 4, 2009

Related U.S. Application Data

(60) Provisional application No. 61/086,010, filed on Aug. 4, 2008.

(51) Int. Cl.
 *G01J 4/00* (2006.01)
(52) U.S. Cl. ........ 356/365; 356/336; 356/337; 356/369; 250/225
(58) Field of Classification Search .................. 348/148, 348/79, 81; 250/225; 356/336–338, 365 356/369
See application file for complete search history.

(56) References Cited

U.S. PATENT DOCUMENTS

| | | | | |
|---|---|---|---|---|
| 4,407,008 | A * | 9/1983 | Schmidt et al. ................. | 348/79 |
| 4,412,246 | A * | 10/1983 | Allen et al. ...................... | 348/79 |
| 4,612,614 | A | 9/1986 | Deindoerfer et al. | |
| 4,902,137 | A * | 2/1990 | Krieg et al. .................... | 356/427 |
| 5,017,497 | A | 5/1991 | de Grooth et al. | |
| 5,087,823 | A * | 2/1992 | Silvy et al. ..................... | 250/225 |
| 5,159,397 | A | 10/1992 | Kosaka et al. | |
| 5,159,398 | A | 10/1992 | Maekawa et al. | |
| 5,247,339 | A | 9/1993 | Ogino | |
| 5,247,340 | A | 9/1993 | Ogino | |
| 5,248,451 | A | 9/1993 | Tsunaga et al. | |
| 5,311,290 | A * | 5/1994 | Olson et al. .................... | 356/634 |
| 5,471,294 | A | 11/1995 | Ogino | |
| 5,650,610 | A * | 7/1997 | Gagnon ......................... | 356/369 |
| 5,850,284 | A * | 12/1998 | Schoeffler et al. ............. | 356/369 |
| 6,028,663 | A | 2/2000 | O'Mongain et al. | |
| 6,067,155 | A * | 5/2000 | Ringlien ....................... | 356/365 |
| 6,115,119 | A * | 9/2000 | Sieracki et al. ................ | 356/337 |
| 7,030,981 | B2 * | 4/2006 | Bishop et al. ................. | 356/365 |
| 7,599,545 | B2 * | 10/2009 | Shibata et al. ................ | 382/141 |
| 8,005,314 | B2 * | 8/2011 | Ortyn et al. .................... | 382/275 |
| 2005/0030373 | A1 * | 2/2005 | Chao et al. ...................... | 348/79 |
| 2006/0177937 | A1 | 8/2006 | Kurabayashi et al. | |

(Continued)

FOREIGN PATENT DOCUMENTS

JP 2000338030 12/2000

OTHER PUBLICATIONS

Oldenbourg, R., Methods in Molecular Medicine: Analysis of Microtubule Dynamics of Polarized Light, Methods Mol. Med. 2007, 137, 111-123, US.

(Continued)

*Primary Examiner* — Ramy M Osman
(74) *Attorney, Agent, or Firm* — Verrill Dana, LLP; Chris A. Caseira

(57) ABSTRACT

An imaging system with an imaging mechanism which includes polarization analyzers, which may be crossed polarization analyzers, positioned to provide birefringence images of particles in the fluid passing through the flow chamber. Captured images are of high resolution and may be used in comparison to known images of a library of images. The system and related method enhance the accuracy and sensitivity of particle monitoring by utilizing birefringence imaging combined with particle analysis and the detection of each particle's characteristic features, such as crystalline features. The system includes a scatter detector used to trigger backlighting of the flow chamber and capture images of particles therein.

14 Claims, 4 Drawing Sheets

U.S. PATENT DOCUMENTS

2006/0197032 A9 9/2006 Oostman et al.
2007/0139541 A1* 6/2007 Fein et al. ................ 348/294
2007/0184471 A1 8/2007 Yguerabide et al.

OTHER PUBLICATIONS

Johnson, L., Enhanced early detection and enumeration of zebra mussel (Drieissna spp.) veligers using cross-polarized light microscopy, Hydrobiologica, 1995, 312, Belgium.

Marie, D. et al., Enumeration of Marine Viruses in Culture and Natural Samples by Flow Cytometry, Applied and Environmental Microbiology, Jan. 1999, vol. 65, No. 1, 45-52, US.

Website page mccroneassociates.com/Techniques/detailasp?TECHNIQUES_ID=19& of McCrone Associates, 1 pp., 2009.

* cited by examiner

SYSTEM AND METHOD FOR MONITORING BIREFRINGENT PARTICLES IN A FLUID

CROSS REFERENCE TO RELATED APPLICATION

The present relates to, and claims the priority benefit of, U.S. Provisional Patent Application No. 61/086,010, filed Aug. 4, 2008, entitled SYSTEM AND METHOD FOR MONITORING ZEBRA MUSSELS IN A FLUID, of the same named inventors. The entire content of that application is incorporated herein by reference.

BACKGROUND OF THE INVENTION

1. Field of the Invention

The present invention relates generally to an optical flow imaging and analysis configuration used in particle analysis instrumentation, and more particularly to a birefringent particle in-flow imaging system configured to enable the accurate identification of particles in a fluid.

2. Description of the Prior Art

The art has seen various optical/flow systems employed for transporting a fluid within an analytical instrument to an imaging and optical analysis area. A liquid sample is typically delivered into the bore of a flow chamber and this sample is interrogated in some way so as to generate analytical information concerning the nature or properties of the sample. For example, a laser beam may excite the sample that is present in the bore of the capillary, with the emitted fluorescence energy representing the signal information.

In the area of identifying birefringent particles, such as crystals, in a fluid, the closest known relevant technological developments involve manual microscope measurements, which is not flow augmented to enable the easy counting and detection of such particles. It would be advantageous to detect with accuracy the existence and density of particles in a flow stream for various reasons. For example, Zebra Mussels are an invasive fresh water mussel species that can foul power plant water intakes and can take over the ecosystem in fresh water lakes and ponds. A flow system such as that described in this document would lend itself to automation in a way that would facilitate the accurate detection of Zebra Mussels and other types of birefringent particles, such as those particles responsive to cross polarization.

The inefficiencies of manually counting particles with a microscope may result in inconclusive counts based on the less than optimum collection of water samples from a pond or lake sample. This microscope method is also tedious and time consuming. It also does not lend itself to easy automation.

SUMMARY OF THE INVENTION

It is an object of the present invention to provide an imaging system arranged to detect with reliable accuracy the existence of particles in a flowing fluid. It is also an object of the present invention to provide such an imaging system that may be incorporated into, or operate in a similar manner as that of, existing particle-in-fluid imaging systems.

These and other objects are achieved with the present invention, which is a system with a detection mechanism that includes polarization analyzers arranged with their polarization axes perpendicular to one another, resulting in the passage of light to a camera only when a particle with detectable birefringence is between the analyzers. The system further includes a video system arranged to image particles in the fluid passing through the flow chamber in response to the trigger signals. Images captured by the video system are of high resolution and may be used in comparison to known particle images of a library of images. Computer programming is created to operate a computing device of the system to match (or recognize non-matching) of captured images with known particle images of the library. Identification of the particles in the flowing fluid may then be made.

The system and related method of the present invention enhances the accuracy and sensitivity of birefringent particle monitoring including, but not limited to, minerals, pharmaceuticals, emulsions, crystals (including crystalline organic structures such as Zebra Mussels) and fibers monitoring, by utilizing imaging systems combined with birefringent particle analysis.

The advantages gained by the invention compared to the state of the art of currently available methods are: 1) more accurate measurements of individual organism counts from scatter signals and birefringence imaging; and 2) better ability to easily monitor for such particles versus conventional manual microscope techniques. These and other advantages of the present invention will become more readily apparent upon review of the following detailed description and the accompanying drawings.

DETAILED DESCRIPTION OF THE PREFERRED EMBODIMENT

Figure 1:
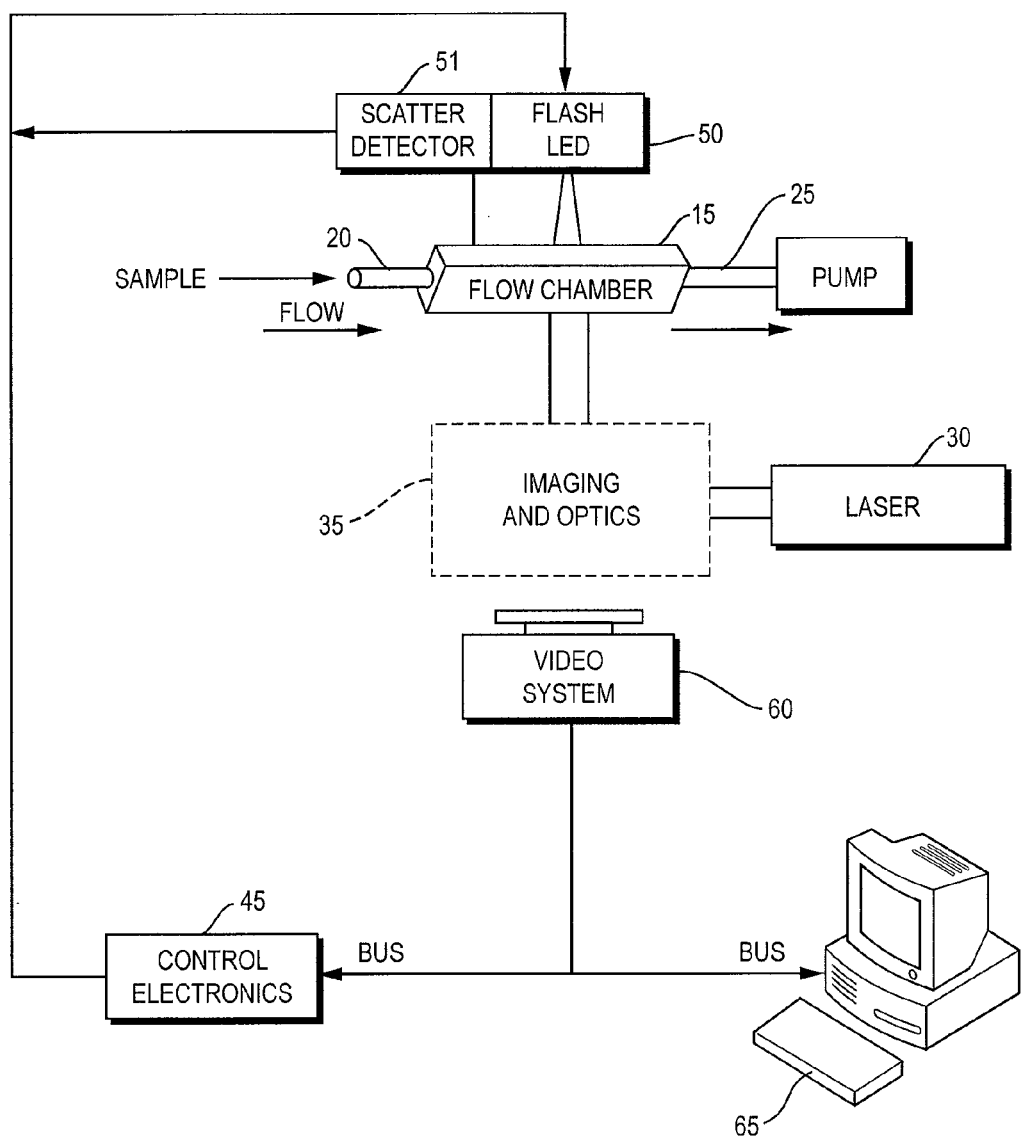
FIG. 1 schematically illustrates a system for studying particles in a fluid according to one embodiment of the invention.
Figure 2:
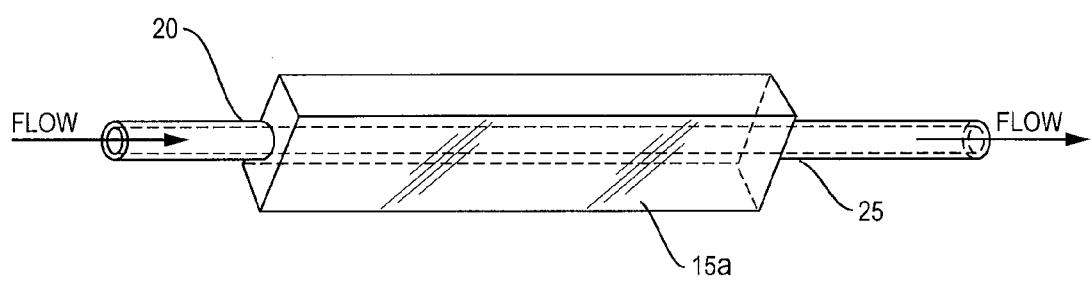
FIG. 2 is an enlarged perspective view of the flow chamber of the system of FIG. 1.

A system 10 of the present invention suitable for high quality automated counting and imaging of particles exhibiting birefringence characteristics and that exist in a fluid is shown in FIGS. 1 and 2. The system 10 includes a flow chamber 15, a light source 30, an imaging and optics system 35, an image detection system 40 including control electronics 45, a backlighting generator 50, an image capturing system 60 and a computing device 65. The combination of these components of the system 10 arranged and configured as described herein enable a user to detect birefringent particles in the fluid and, specifically, to enhance the accuracy and sensitivity of such detection.

The flow chamber 15 includes an inlet 20 for receiving the particle-containing fluid to be observed, and an outlet 25 through which the fluid passes out of the flow chamber 15 after imaging functions have been performed. The flow chamber 15 may be fabricated of a material suitable for image capturing, including, for example, but not limited to, transparent microscope glass or rectangular glass extrusions. The flow chamber 15 may be circular or rectangular in shape. The flow chamber 15 defines a channel 15a through which the fluid flows at a predetermined selectable rate. The channel 15a may be of rectangular configuration. The length and width of channel 15a are selected to roughly match the field of view of the imaging optics 35. This keeps all of the particles flowing through the flow chamber in focus, removing the need for a focusing sheath flow, and thereby enabling accurate counting of cells while retaining imaging capability. The inlet 20 of the flow chamber 15 is connectable to a fluid source and the outlet 25 is connectable to a downstream means for transferring the fluid away from the flow chamber 15.

Figure 3:
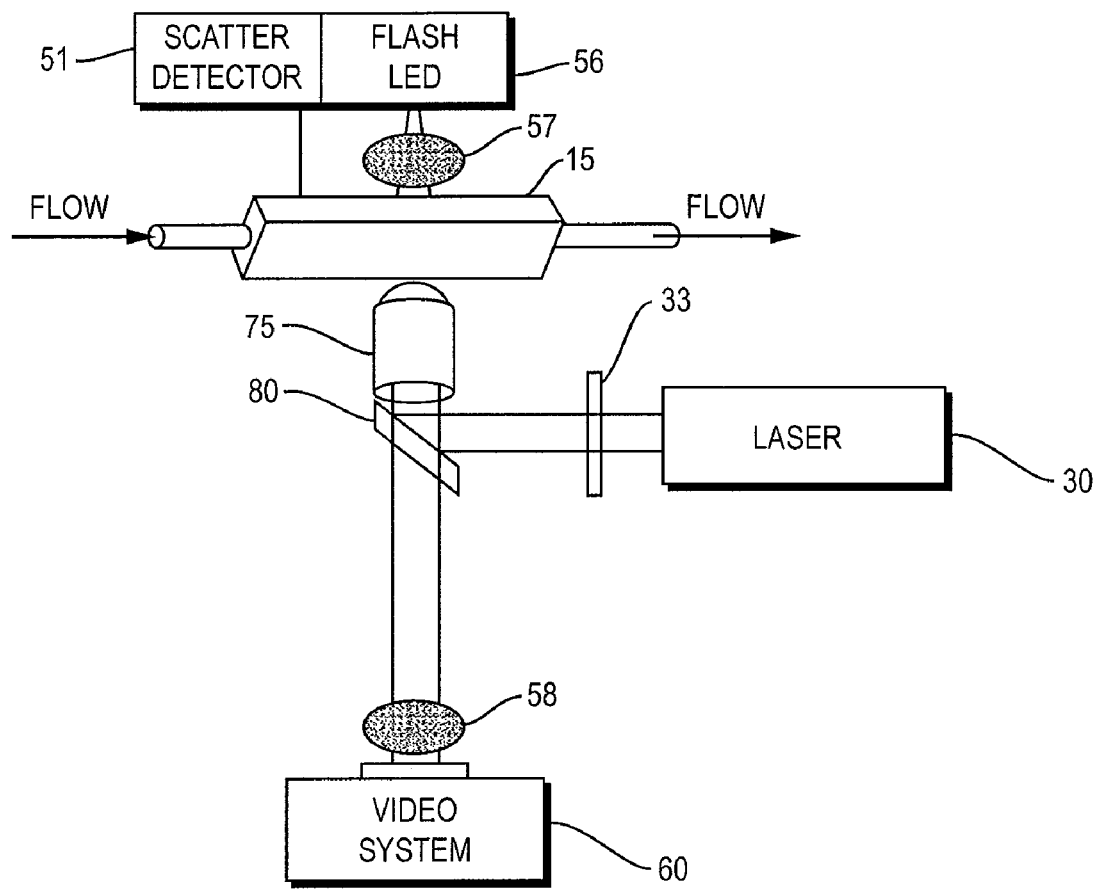
FIG. 3 is a detailed schematic illustration of the plurality of detectors and associated filters for capturing distinct birefringence images of particles within a flowing fluid.

With reference to FIGS. 1 and 3, the light source 30 is used to generate scatter excitation light which is passed through the optics and imaging system 35 to the flow chamber 15, resulting in light scatter by particles located in the fluid. The light source 30 may be a laser with a wavelength filter 33. The laser 30 may be, but is not limited to being, a 470 nanometer (nm), 488 nm or 532 nm solid state model laser available from an array of manufacturers known to those of skill in the art. The filter 33 should at least have the characteristic of being able to transmit light at the wavelengths of light generated by the laser 30. An example of a suitable form of the filter 33 is a 532/10X filter of the type that can be used with a 532 nm laser available from Chroma Technologies of Rockingham, Vt. US; those of skill in the art will recognize that other suitable filters may be employed for the filter 33. Dichroic mirror 80 blocks laser reflections from the flow chamber 15 and allows wavelengths of light longer than that of the laser 30 to the imaging section of the system 10. An example of a suitable filter which will work with a 532 nm laser is a 505DCLP longpass filter from Chroma Technologies.

With continuing reference to FIGS. 1 and 3, the imaging and optics system 35 includes a microscope objective 75 to image the particle flow onto the image capturing system 60 and focus excitation light from the light source 30 onto the flow chamber 15. The control electronics 45 may be configured to receive input signals and produce output information compatible with the specific needs of the user of the system 10. An example of a suitable electronics system capable of performing the signal activation and output information associated with the control electronics 45 of the system 10 is the detection electronics described in U.S. Pat. No. 6,115,119, the entire content of which is incorporated herein by reference. Those of ordinary skill in the art will recognize that the specific electronics system described therein may be modified, such as through suitable programming for example, to trigger desired signal activation and/or to manipulate received signals for desired output information.

The light source 30 may be operated to transmit light periodically, sporadically, or regularly. For example, the light source may emit light signals and a scatter detector 51 may be employed on the back side of the flow chamber 15 to detect changes in light signals from the light source, such as when a particle passing through the flow chamber 15. The scatter detector 51 may be any type of suitable device capable of detecting variations in received light and transmitting electrical signals indicative of the light variations. In one embodiment, the scatter detector 51 may be an array of photoreceptive sensors. The scatter detector 51 is coupled to the control electronics 45 to signal to the control electronics the light change indicative of the existence of a particle in the flow chamber 15. The control electronics 45 is coupled to the computing device 65. The computing device 65 is programmed to store the information received from the control electronics 45 and to make calculations and processing decisions based on the information received. The computing device 65 may be any sort of computing system suitable for receiving information, running software programs on its one or more processors, and producing output of information, including, but not limited to images and data, that may be observed on a user interface.

The control electronics 45 is also coupled, directly or indirectly through the computing device 65 to the backlighting generator 50. In particular, the control electronics 45 and the computing device 65 are arranged to generate a trigger signal to activate the backlighting generator 50 to emit a light flash upon detection of a particle or particles in the flow chamber 15. That is, the trigger signal generated produces a signal to activate the operation of the backlighting generator 50 so that a light flash is generated. Specifically, the backlighting generator 50 may be a Light Emitting Diode (LED) flash or other suitable light generating means that produces a light of sufficient intensity to backlight the flow chamber 15 and image the passing particles. The LED flash may be a 670 nm LED flash, or a flash of another other suitable wavelength of high intensity, which is flashed on one side of the flow chamber 15 for 200 µsec (or less). At the same time, the image capturing system 60 positioned on the opposing side of the flow chamber 15 is activated to capture an instantaneous image of the particles in the fluid as "frozen" when the high intensity flash occurs. Polarization analyzers 57 and 58 are deployed in the image path to modify the display of the particles located in the flow chamber 15.

In one embodiment of the invention, the polarization analyzers 57 and 58 are crossed, meaning that under normal conditions, light filtered by analyzer 57 is polarized perpendicular to the polarization axis of analyzer 58 so little or no light can pass through 57 and then through 58. The polarization analyzers 57 and 58 only allow light to reach the image capturing system 60 if it passes through particles, that is, birefringent particles, and has its polarization rotated or changed from linear to elliptical polarization. This is a very specific property of certain particles but is not applicable with respect to all particles. For example, it is suitable for use in detecting Zebra Mussels due to the calcite composition of its shells. More generally, for certain materials, the application of incident waves of different polarization will produce different indexes of refraction. This birefringence characteristic can be easily captured and used to identify a particular material in the fluid through the present invention since the birefringent particles will appear to glow with light when the water is imaged. The polarization analyzers 57 and 58 may be GT10B linear polarization analyzers available from Thorlabs of Newton, N.J. Those of ordinary skill in the art will recognize that suitable polarization analyzers may be used that are not crossed while still producing the birefringence information of interest in the detection of the existence of the particular material or materials of interest in the fluid.

The image capturing system 60 is arranged to either retain the captured image, transfer it to the computing device 65, or a combination of the two. The image capturing system 60 includes characteristics of a digital camera or an analog camera with a framegrabber or other means for retaining images. For example, but in no way limiting what this particular component of the system may be, the image capturing system 60 may be, but is not limited to being, a CCD firewire, a CCD USB-based camera, or other suitable device that can be used to capture images and that further preferably includes computing means or means that may be coupled to computing means for the purpose of retaining images and to manipulate those images as desired. The computing device 65 may be programmed to measure the size and shape of the particle captured by the image capturing system 60 and/or store the data for later analysis.

The images captured by the image capturing system 60 and stored with the computing device 65 may be analyzed and compared to known images of particles including, for example, Zebra Mussels. When a trigger is generated (i.e., a light scattering particle is detected), software scans the resulting image, separating the different particle sub-images in it. The area of each particle is measured by summing the number of pixels in each particle image below a selectable threshold and multiplying the result by the equivalent physical area of a pixel. This computed area of the particle is stored in a spreadsheet-compatible file along with other properties of the particle, e.g., its measured peak fluorescence, time of particle passage, and the location of the particle in the image. The sub-image of each particle is copied from the chamber image and saved with other sub-images in a collage file. Several of these collage files may be generated for each system experiment. A special system file is generated, containing the collage file location of each particle sub-image, particle size and time of particle passage.

The software is written to generate two data review modes: (1) image collage and (2) interactive scattergram. In the image collage mode, the user may review a series of selectable sub-images in a collage file. Reviewing these files allows the user to identify particle types, count particles, or study other features. In interactive scattergram mode, data is presented to the user as a dot-plot; e.g., a graph of particle size. If the user selects a region of the scattergram, images of particles having the characteristics plotted in that region are displayed on a display of the computing device 65, allowing the user to study particle populations and to examine images of particles with specific sizes, such as cells of a specific type. Because a spreadsheet compatible file is generated for each review, the user may also review the data with a spreadsheet program. This information allows the user to readily generate cell counts and scatter and size distribution histograms for each sample. This file also contains the location of each particle in the original image which is used to remove redundant data from particles that have become attached to the flow chamber 15.

Figure 4:
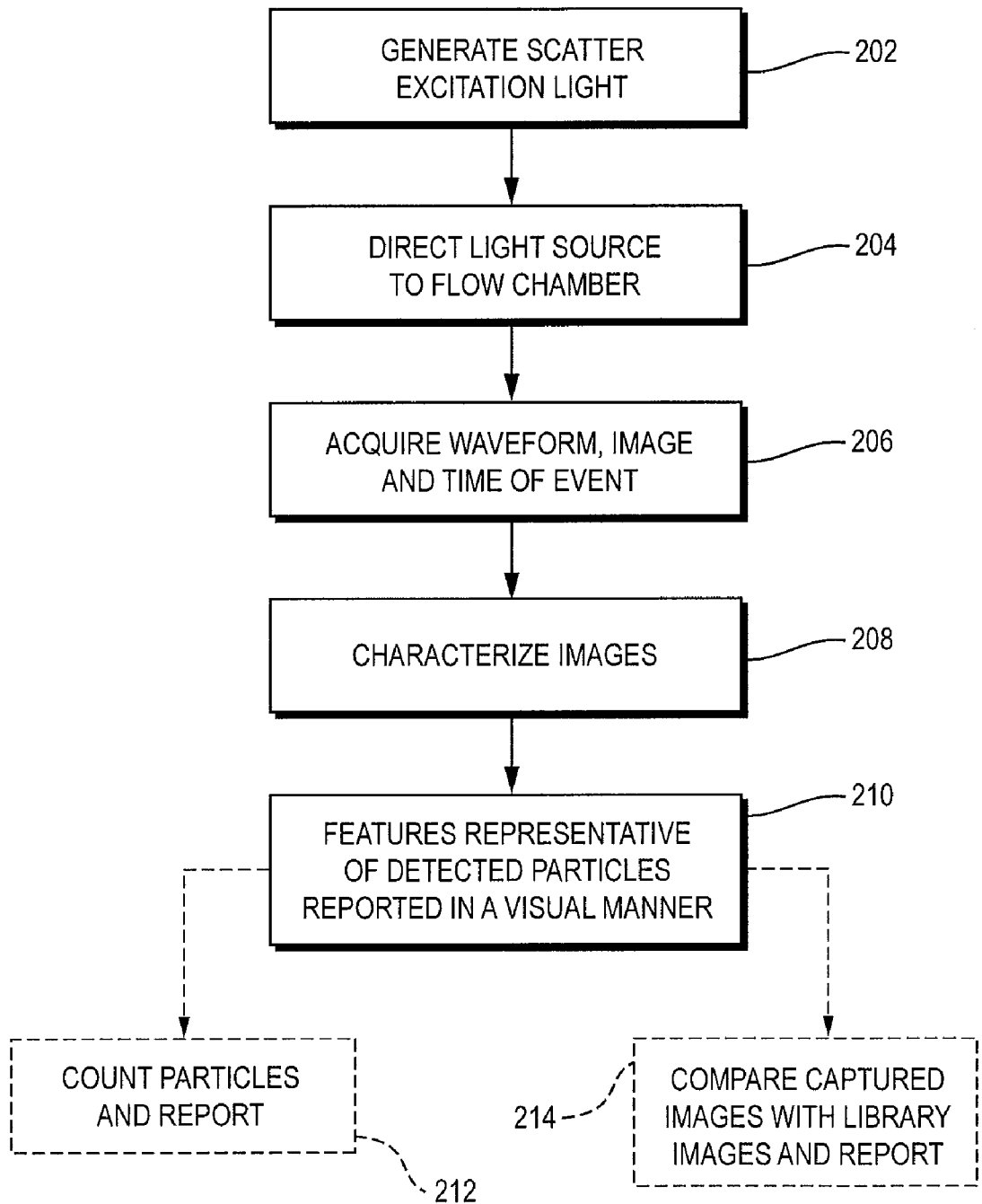
FIG. 4 is a flow diagram representing steps to be carried out using the computing device and associated programming of the present invention.

As represented in FIG. 4, a method 200 of the present invention embodied in one or more computer programs, includes steps associated with storing and analyzing images captured with the system 10 of the present invention. In the first step, step 202, the light source 30 and imaging optics 35 generate scatter excitation light, which is directed to the flow chamber 15 within which a fluid to be monitored passes, step 204. The detection system 40 including the control electronics 45 is used to detect separately, images associated with the light waveforms scattered from particles in the flow chamber 15. The detected images are transferred to the computing device 65 for storage and analysis, step 206. The images captured are characterized based on particle shape and size, in addition to other information of interest, step 208. Features representative of the birefringent particles in the fluid may be detected and that information may be reported in a visual manner, step 210. For example, the information may be presented in graphic representations, spreadsheet lists, or combinations thereof. Optionally, the acquired image information may be used to count the number of particles in the fluid sample observed and reported, step 212, and/or the captured images may be compared to known images of particles of interest and reported, step 214.

It is to be understood that the computing device 65 used to gather the captured image information and to perform calculations and observe features of the captured image information may be associated with local or remote computing means, such as one or more central computers, in a local area network, a metropolitan area network, a wide area network, or through intranet and internet connections. The computing device 65 may include one or more discrete computer processor devices. The computing device may include computer devices operated by a centralized administrative entity or by a plurality of users located at one or more locations.

The computing device 65 may be programmed to include one or more of the functions of the system 10. The computing device 65 may include one or more databases including information related to the use of the system 10. For example, such a database may include known images of example particles of interest. The database may be populated and updated with information provided by the user and others.

The steps of the method 200 described herein and additional steps not specifically described with respect to FIG. 4 but related to the use of the system 10 may be carried out as electronic functions performed through the computing device 65 based on computer programming steps. The functions configured to perform the steps described herein may be implemented in hardware and/or software. For example, particular software, firmware, or microcode functions executing on the computing device 65 can provide the trigger, image capturing and image analysis functions. Alternatively, or in addition, hardware modules, such as programmable arrays, can be used in the devices to provide some or all of those functions, provided they are programmed to perform the steps described.

The steps of the method 200 of the present invention, individually or in combination, may be implemented as a computer program product tangibly as computer-readable signals on a computer-readable medium, for example, a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual Basic, C, or C++, Fortran, Pascal, Eiffel, Basic, COBOL, and the like, or any of a variety of combinations thereof. The computer-readable medium on which such instructions are stored may reside on one or more of the components of system 10 described above and may be distributed across one or more such components. Further, the steps of the method represented in FIG. 4, may be performed in alternative orders, in parallel and serially.

The system 10 of the present invention allows much greater sensitivity to birefringent particles due to individual particle measurements and verification of each particle with imaging. A specific example use of this invention involves the monitoring of Zebra Mussels in ponds and lakes. More generally, the system 10 may be used to detect and analyze minerals, pharmaceuticals, emulsions, crystals and fibers, as well as any other type of structure with characteristics enabling birefringence analysis. As previously described, the invention is carried out by combining polarization analyzers with an imaging system and configuring the computing device 65, through software to image the particle birefringence and then using known imaging capabilities to count and/or identify the particles, if desired.

One or more example embodiments to help illustrate the invention have been described. Nevertheless, it will be understood that various modifications may be made without departing from the spirit and scope of the invention.

What is claimed is:

1. A system for imaging birefringent particles in a flowing fluid, the system comprising:

a. a flow chamber including a channel arranged to transport the flowing fluid therethrough at a selectable rate;

b. a light source arranged to generate scatter excitation light to illuminate birefringent particles in the flowing fluid in the flow chamber;

c. a backlighting generator arranged to produce a light of sufficient intensity to backlight the flow chamber;

d. a microscope objective arranged to focus light from the light source onto the flow chamber;

e. a scatter detector to detect changes in the light from the light source indicative of the existence of one or more particles in the flow chamber;

f. control electronics configured to receive signals from the scatter detector, wherein the control electronics are coupled to the backlighting generator and configured to activate the operation of the backlighting generator;

g. an image capturing system including a camera to capture images of the birefringent particles in the fluid, a first polarization analyzer and a second polarization analyzer, wherein the first and second polarization analyzers are arranged in a cross polarization configuration to permit the passage of light to the camera only when the birefringent particles with detectable birefringence pass between the first and second polarization analyzers; and h. a computing device to receive signals from the control electronics and the image capturing system and to output information about the birefringent particles detected in the flowing fluid.

2. The system of claim 1 wherein the first and second polarization analyzers of the image capturing system are arranged with their axes perpendicular to one another.

3. The system of claim 1 wherein the camera includes a digital or analog camera and a framegrabber.

4. The system of claim 1 wherein the light source is a laser with an excitation filter.

5. The system of claim 1 wherein the backlighting generator is arranged to generate a high intensity flash.

6. The system of claim 5 wherein the backlighting generator is a light emitting diode flash.

7. The system of claim 1 wherein the computing device includes a database to store data and images associated with detected particles and software to generate with the computing device particle data as image collages and interactive scattergrams.

8. A method for imaging birefringent particles in a flowing fluid, the method comprising:

a. transporting the flowing fluid through a channel of a flow chamber at a selectable rate;

b. generating scatter excitation light to illuminate the flowing fluid in the flow chamber;

c. detecting scattered light signals indicative of the existence of one or more birefringent particles in the flow chamber;

d. backlighting the flow chamber upon detection of scattered light signals;

e. cross polarizing with a first polarization analyzer and a second polarization analyzer light from the backlighting of the flow chamber to permit only light passing through the birefringent particles to pass to a camera to capture images; and f. outputting information about the birefringent particles detected in the flowing fluid based on captured images thereof.

9. The method of claim 8 wherein the step of cross polarizing light includes placing the first polarization analyzer and the second polarization analyzer with their polarization axes perpendicular to one another in relation to the flow chamber so that light passes to the camera only when the birefringent particular pass between the first and second polarization analyzers.

10. The method of claim 8 wherein the camera is a digital or analog camera and a framegrabber.

11. The method of claim 8 wherein the step of generating scatter excitation light is achieved with a laser and an excitation filter.

12. The method of claim 8 wherein the step of backlighting the flow chamber is achieved using a backlighting generator arranged to generate a high intensity flash.

13. The method of claim 12 wherein the backlighting generator is a light emitting diode flash.

14. The method of claim 8 further comprising the steps of storing data and images associated with detected particles and generating particle data as image collages and interactive scattergrams.

* * * * *